United States Patent [19]

Jarque et al.

[11] 4,172,894
[45] Oct. 30, 1979

[54] 3-THIENYL-3-METHYL-4-PENTYL-2-PYRIDYL-KETONE

[75] Inventors: Ricardo G. Jarque; Juan B. Cartes, both of Barcelona; Francisco L. Calahorra, San Juan Despi; Cristóbal M. Roldán; Fernando R. Peinado, both of Madrid, all of Spain

[73] Assignee: Laboratories Made, S.A., Madrid, Spain

[21] Appl. No.: 915,434

[22] Filed: Jun. 14, 1978

[30] Foreign Application Priority Data

Jun. 20, 1977 [ES] Spain ............................... 459924

[51] Int. Cl.² .................... A61K 31/44; C07D 409/02
[52] U.S. Cl. ............................... 424/263; 546/284
[58] Field of Search ................ 260/294.8 D; 424/263; 546/284

[56] References Cited

U.S. PATENT DOCUMENTS 3,408,358  10/1968  Hardimann et al. ......... 260/294.8 D Primary Examiner—Alan L. Rotman
Attorney, Agent, or Firm—Ladas, Parry, Von Gehr, Goldsmith & Deschamps

[57] ABSTRACT

3-Thienyl-3-methyl-4-pentyl-2-pyridyl-ketone of the formula:

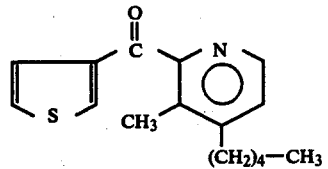

useful as an analgesic and a process for its preparation are disclosed.

3 Claims, No Drawings

3-THIENYL-3-METHYL-4-PENTYL-2-PYRIDYL-KETONE

This invention relates to obtaining 3-thienyl-3-methyl-4-pentyl-2-pyridyl-ketone of formula I, and its addition salts with pharmacologically acceptable acids, for example hydrochloride.

Compound I is a new substance of use as an analgesic, and according to the method of the invention it is obtained by reaction, carried out with excess butyl bromide proceeding from the preparation of butyl-lithium, between the 3-thienyl-lithium (A) recently prepared by the action of the butyl-lithium on the 3-bromothiophene at the temperature of $-70°$ C., and 2-cyane-3,4-dimethylpyridine (B), a compound described in Spanish Patent Application No. 435,984 of the applicant firm, in which a process for its preparation is claimed.

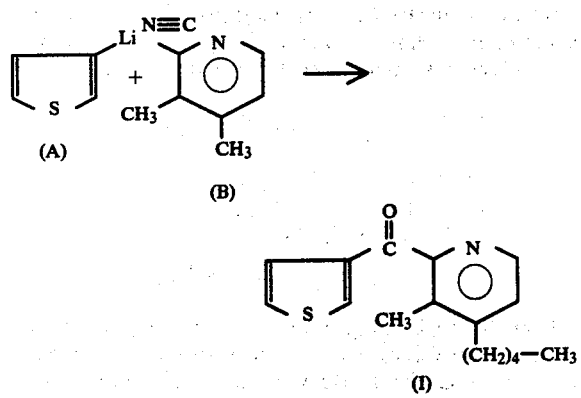

The reaction commences at the temperature of $-70°$ C. and in inert atmosphere with rapid addition of 2-cyane-3,4-dimethylpyridine dissolved in an anhydrous solvent over the 3-thienyl lithium ether solution containing an excess of butyl bromide proceeding from the preparation of the butyl-lithium, the temperature of the mixture being raised immediately to $-10°$ C. and so maintained for 45 minutes. After hydrolizing the resulting mixture with hydrochloric acid and alkalinizing the resulting aqueous layer with NaO$_H$, it is extracted with an organic solvent. The ketone (I) is purified by chromatography in a silica gel column and is characterized in the form of the hydrochloride.

The following example is given only as an illustration and in no case must be considered limitative of the invention.

EXAMPLE

Obtaining 3-thienyl-3-methyl-4-pentyl-2-pyridyl-ketone

Addition is made to 265 ml of a 1.36 N ether solution of butyl-lithium recently prepared from excess lithium and butyl bromide cooled to $-70°$ C. of 58.6 g of 3-bromothiophene dissolved in 360 ml of anhydrous ether, care being taken that the temperature of the mixture does not exceed $-70°$ C. Following the addition the mixture is stirred for 10 min. and drop by drop addition is made of 29 g of 2-cyane-3,4-dimethylpyridine, dissolved in 40 ml of anhydrous benzene, during 40 min.; the mixture is stirred for 45 min., the temperature being allowed to rise spontaneously, and the mixture is then brought to boil and is boiled for 30 min., following which the reaction mixture is externally cooled. It is acidified with 50% hydrochloric acid, the ether layer is distilled off, the resulting aqueous layer is boiled for two hours, is cooled, the mixture is washed with ether and is basified with 40% sodium hydroxide. The reaction mixture is extracted with ether, the ether layer is dried and evaporates to dryness to thus produce a black oil which is distilled, the fraction made between 140° and 170° C. at 0.8 mm Hg being collected. The oil thus obtained is subjected to chromatography in silica gel column, 6 g of 3-thienyl-3-methyl-4-pentyl-2-pyridyl ketone being obtained upon evaporation to dryness of the fractions eluted with 20/80 petroleum/benzene ether. Yield is 10%. From an analytical sample the hydrochloride was precipitated, which crystallized from anhydrous acetone gave a melting point of $145°-148°$ C. Calculated analysis for $C_{16}H_{20}NSOCl$: C, 62.02; H, 6.50; N, 4.52; S, 10.35. Found: C, 61.75; H, 6.83; N, 4.65; S, 10.01.

THE PHARMACOLOGICAL PROPERTIES OF THE PRODUCT OF THE INVENTION

The product is one of analgesic activity. Its toxicity and activity have been compared with those of dextropropoxyphene.

A—ACUTE TOXICITY

Acute toxicity study was made in Swiss I.C.R. albino mice of both sexes of $30\pm2$ g of weight, kept without food for 24 hours prior to the experiment. Ambient temperature and relative humidity were kept constant. The products were administered intraperitoneally, and 48 hours after treatment the number of deaths was counted. Calculation of the lethal dose ($LD_{50}$) was made by the Litchfield-Wilcoxon test. The results obtained were:

TABLE I

| Product | $LD_{50}$ (mg/kg) |
|---|---|
| I | 717.5 |
| Dextropropoxyphene | 140 |

B—ANALGESIC ACTIVITY

1. Thermal analgesia

The thermal analgesic effect was studied in Swiss I.C.R. albino mice. The 55° C. "hot plate" technique was used. Batches of 10 mice were made.

The products in study were administered intraperitoneally and after 30 minutes the mice were placed on the "hot plate", note having been made, in seconds, of the time it took them to jump. Batches of control animals were injected with only distilled water.

The results are shown in Table II.

TABLE II

| Treatment | Dose mg/kg | Jumping time in sec. $\bar{x}$ ± S.E.M.[1] | Signif. of Differences Dextroprop. | Control |
|---|---|---|---|---|
| Control | — | 38 ± 4.253 | — | — |
| Dextroprop. | 30 | 83.7 ± 12.267 | — | p<0.005 |
| Prod. I | 30 | 96.7 ± 9.771 | N.S. | p<0.0001 |

[1]The analgesic activity of Product I is not significantly different from that of dextropropoxylene.

2. Chemical Analgesia

The analgesic effect was studied in Swiss I.C.R. albino mice with the acetic acid writhing technique. Batches of 10 mice were made.

The products in study were administered intraperitoneally, and 30 minutes later 0.25 ml of 1% acetic acid were injected intraperitoneally. A batch of control animals received only the acetic acid. Twenty minutes following administration of the acetic acid, the number of writhes in each mouse is counted.

The results are shown in Table III.

TABLE III

| Treatment | Dose mg/kg | No. of writhes $\bar{x} \pm$ S.E.M.[1] | Signif. of Differences Control | Dextroprop. |
|---|---|---|---|---|
| Control | — | 121.5 ± 7.184 | — | — |
| Prod. I | 25 | 35.75 ± 7.639 | p<0.00005 | p<0.02 |
| Dextroprop. | 25 | 62.8 ± 6.991 | p<0.00005 | — |

[1]Product I has analgesic activity significantly superior to that of dextropropoxyphene.

We claim:

1. A process for obtaining 3-thienyl-3-methyl-4-pentyl-2-pyridyl-ketone of formula I

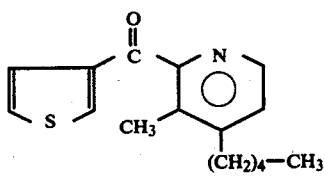

which comprises the steps of reacting 3-thienyl-lithium of the formula

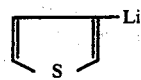

recently prepared by the action of the butyl-lithium on the 3-bromothiophene at the temperature of −70° C., with 2-cyane-3,4-dimethylpyridine of the formula

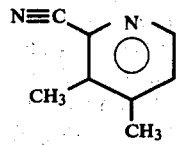

in an excess of butyl bromide proceeding from the preparation of the butyl-lithium, and in that after hydrolysis in acid medium isolation can be made of the compound I, which is purified by chromatography in silica gel column and is characterized in form of hydrochloride.

2. 3-thienyl-3-methyl-4-pentyl-2-pyridyl-ketone I

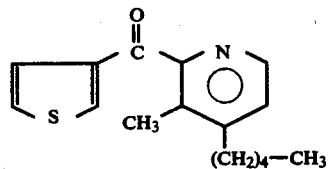

3. An analgesic composition which comprises a therapeutically effective amount of the compound of claim 2 as active ingredient, along with a pharmaceutically acceptable carrier.

* * * * *